United States Patent [19]

Ikeda et al.

[11] Patent Number: 4,922,597
[45] Date of Patent: May 8, 1990

[54] BOX FOR DISPOSING OF USED INJECTION NEEDLES

[75] Inventors: Kohji Ikeda, Osaka; Akira Tsuji, Kishiwada; Yoshiyuki Sunaga, Kiryu, all of Japan

[73] Assignees: Nissho Corporation; Fujisawa Pharmaceutical Company, Ltd., both of Osaka, Japan

[21] Appl. No.: 251,460

[22] Filed: Sep. 30, 1988

[30] Foreign Application Priority Data

Oct. 1, 1987 [JP] Japan .................. 62-249345
Mar. 25, 1988 [JP] Japan .................. 63-72402

[51] Int. Cl.⁵ .............................................. B65D 25/00
[52] U.S. Cl. ........................................ 29/240; 206/366
[58] Field of Search ............... 206/365, 366; 128/917; 29/290, 290.5, 239, 280, 282

[56] References Cited

U.S. PATENT DOCUMENTS 4,466,538  8/1984  Gianni .
4,552,280 12/1985  Owen et al. .
4,738,362  4/1988  Burns et al. ..................... 206/366
4,807,344  2/1989  Kelson et al. ..................... 29/240

FOREIGN PATENT DOCUMENTS 60-45361  3/1985  Japan .
2192382   1/1988  United Kingdom .

Primary Examiner—Robert C. Watson
Attorney, Agent, or Firm—Oblon, Spivak, McClelland, Maier & Neustadt

[57] ABSTRACT

A box for disposing of used injection needles comprising a case having an opening whereinto a tip portion of a syringe is inserted, a movable member, and a fixed member, both members being arranged in the case. A hub of an injection needle inserted through the opening of the case is firmly held by holding portions of movable member and fixed member due to elasticity of the hub itself. The rotation of the syringe causes the injection needle to be removed from the syringe, and the removed injection needle, which is not pulled out together with the syringe and remains in the holding portions due to holding effect of the holding portions, can be dropped into the case by the operation of a rod outside the case.

4 Claims, 11 Drawing Sheets

BOX FOR DISPOSING OF USED INJECTION NEEDLES

BACKGROUND OF THE INVENTION

The present invention relates to a box for disposing of used injection needles, and more particularly to a box for disposing of used injection needles capable of easily and surely removing used injection needles from syringes without injuring fingers and the like, and capable of safely and hygienically discarding used injection needles together with the box. The box can be preferably used for containing and discarding screw-type double-edged injection needles (such an injection needle that is fixed to a syringe by means of a screw at its hub and has two needle points at both ends, i.e. on the sides of human body and liquid drug) such as dental injection needles.

Hitherto, there have been frequently employed, for dental anesthetic needles, screw-type double-edged injection needles. These types of injection needles are recently almost disposable. At present the used injection needle is covered with a cap or container (hereafter referred to as "cap"), and removed from a syringe together with the cap after releasing a connection (screw connection) with the syringe. Then the injection needle contained in the cap (i.e. covered with the the cap) is put into a suitable case or bag and discarded with the case or bag.

Though the operation of inserting an injection needle into a cap is seemingly easy an accident is likely to happen, while disposing of a large number of injection needles in a day, in that a handler's finger can be injured by the injection needle due to slip of the hand and the like. Such a mistake not only causes damage to the finger and pain to a handler (such as physician and nurse) due to the injection needle, but also involves a very serious danger that the disposer is sometimes infected with virus such as hapatitis B and AIDS (Acquired Immunodeficiency Syndrome) since the injection needle is inserted into the the human body of a patient.

Further, a cap sometimes comes off by mere chance although a used injection needle is covered with a cap. Accordingly, there is a danger, when carrying injection needles encased in a bag, that arms or legs of a carrier are injured by injection needles piercing the bag.

Accordingly, it is an object of the present invention to provide a box for disposing of used injection needles capable of safely and easily removing used injection needles, particularly double-edged injection needles such as dental injection needles, and capable of disposing of them.

SUMMARY OF THE INVENTION

The present invention consists of two inventions, i.e. the first invention and the second invention, which have the common object described above.

In accordance with the first invention, there is provided a box for disposing of used injection needles comprising (A) a case having an opening at its upper or side surface whereinto a tip portion of a syringe is capable of being inserted, and (B) an injection-needle-detaching means which is arranged in the case, and which removes an injection needle from the syringe inserted through the opening and drops into the case;

characterised in that the injection-needle-detaching means comprises (a) a movable member having one holding portion for holding a hub of the injection needle, (b) a fixed member having the other holding portion for holding the hub of the injection needle in cooperation with the movable member and fixed to the case, (c) an elastic means arranged in such a manner that the direction of elastic force thereof is parallel to the moving direction of the movable member, one end of the elastic means being fixed to or contacted with the movable member, and (d) a rod for moving the movable member against the elastic force of the elastic means, a part of the rod protruding outside the case, a holding portion defined by the movable member and the fixed member fits the shape of the hub and forms an opening of which size is a little smaller than that of a cross section of the hub, and a notch continuing to the other holding portion of the fixed member is formed at the fixed member to allow the movement of the hub, which is removed from the syringe and held by the holding portion, together with the movable member.

In the box for disposing of used injection needles according to the first invention, the injection-needle-detaching means provided in the case has a holding portion of which shape fits the shape of a hub of the injection needle. The injection needle inserted into the case through an insertion opening made in the case is firmly held by the holding portion, since the size of the opening defined by the holding portion is a little smaller than that of a cross section of the hub and the hub itself has elasticity. The rotation of the syringe releases the connection between the syringe and the injection needle. The injectin needle removed from the syringe remains held by the holding portion, and moves along a notch formed at the fixed member together with the movable member, while contacting with the fixed member, by moving the movable member forming a part of the holding portion against elastic force of the elastic means. Then the injection needle stops contacting with the fixed member and drops into the case.

In accordance with the second invention, there is provided a box for disposing of used injection needles comprising (A) a tubular guide hole provided laterally at a box and enabling the insertion of a tip portion of a syringe, (B) a slit formed at an under surface of the guide hole and enabling the drop of an injection needle, (C) a holding means for holding a hub of the injection needle screwed at a tip portion of the syringe, the means comprising a fixed member and a movable member and being located at the inner part of the guide hole, (D) an operation rod for pushing and moving the movable member to release the holding condition, a tip of the rod protruding outside the case, and (E) a cap capable of alternatively engaging with the tip of the operation rod and an opening of the tubular guide hole.

According to the second invention, the injection needle is unscrewed from the syringe by inserting the syringe into the tubular guide hole, and by manually rotating the syringe anticlockwise while holding a hub of the injection needle with the holding means to prevent the rotation of the hub. A push of the operation rod releases the holding condition by the fixed member and movable member, whereby the injection needle held by the holding means drops into the case. In that case, the injection needle even in the case of double-edged injection needle can smoothlly drop into the case without being caught by any portion in the case since a slit is formed at the under surface of the guide hole, so that the removal of the injection needle can be easily carried out.

After the case is filled with used injection needles, the cap at the tip of the operation rod is detached from the rod and inserted into the opening of the guide hole. Then the box can be disposed of safely because the opening of the box is perfectly closed and therefore injection needles in the box never goes out of the box.

DETAILED DESCRIPTION

Now there is described a box for disposing of used injection needles (hereafter referred to as "disposing box") of the present invention based on the accompanying drawings.

First a disposing box of the first invention is explained. The disposing box of the first invention is composed of a case 1 and an injection-needle-detaching means (hereafter referred to as "detaching means") arranged in the case 1. The detaching means is composed of an elastic means 6, a movable member 3, a rod 7, and a fixed member 4. Each element is explained in detail below.

The case 1 serves to contain used injection needles removed from syringes. Though the size and shape of the case 1 are not particularly limited in the present invention, the case 1 preferably has a size and shape suitable for holding with one hand when an injection needle is removed from a syringe by the method mentioned later wherein the case 1 is held with one hand and the injection needle is inserted into an insertion opening 2 made in the case 1 with the other hand. In practice, however, the handler is often obliged to remove injection needles with only one hand. In that case, the case 1 is fixed to a suitable position in the room, so that the size and shape thereof might be determined optionally regardless of the size and shape suitable for the holding with one hand described above.

An opening 2 for the insertion of a used injection needle is made on the upper or side surface of the case 1. The position of the insertion opening 2 is not particularly limited and might be made on such a position that the handler can easily insert injection needles. In the embodiment shown in FIGS. 1 to 3, the insertion opening 2 is made on the upper surface (shown by symbol P in FIGS. 1 to 3) of thecase 1. The size of the insertion opening 2 might be suitably determined in consideration of the thickness of a tip portion of a syringe 20 (see FIG. 5). In shot, the size of the insertion opening 2 is so determined as to allow the insertion of the syringe 20 to such a position that a hub 22 of the injection needle 21 can be firmly positioned in an opening 12 defind by a movable member 3 and a fixed member 4 and can be held by both members 3,4.

As a material for the case 1, there can be preferably used acrylonitrile-butadiene-styrene copolymer, polypropylene, polyethylene, polycarbonate, polystyrene, polyacetal, polyamide, vinyl chloride resin and the like. A transparent or semitransparent case is preferable because of assuring ascertainment of the contained used injection needles from outside the case. The case 1 is composed of two or more portions, and is assembled by a suitable combining or connecting method such as heatsealing, ultrasonic sealing and adhering, depending on the material of the case 1 after arranging a movable member 3, elastic means 6, rod 7 and fixed member 4 at prescribed positions in the case 1.

Figure 1:
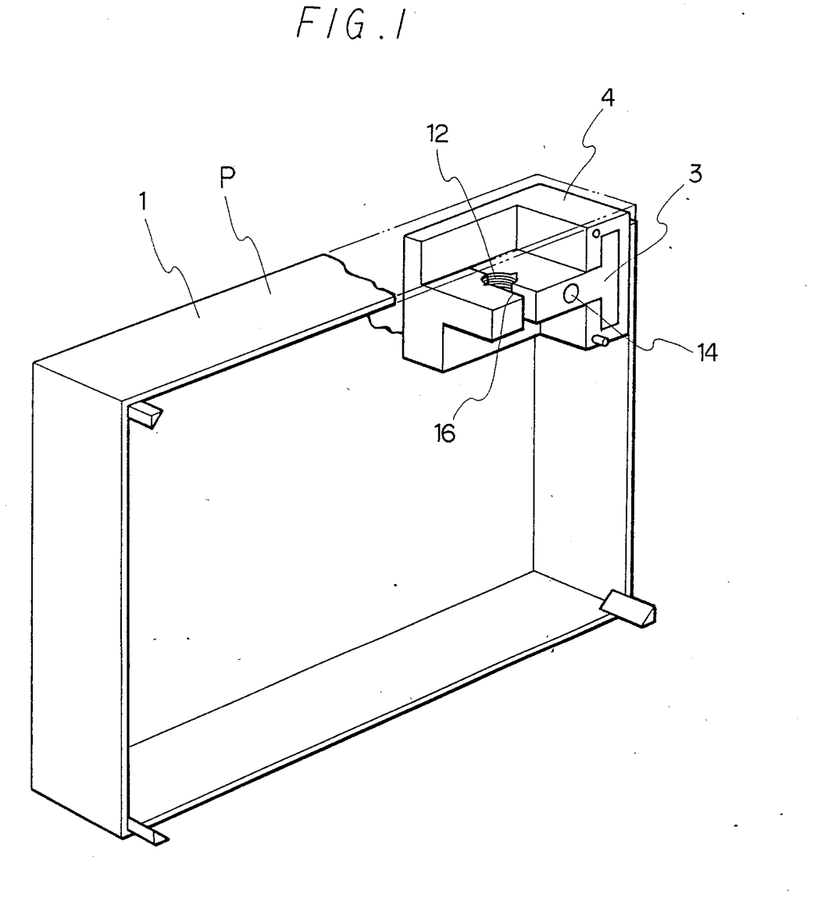
FIG. 1 is a partially-cutaway schematic perspective view showing a complementary half of an embodiment of a box for disposing of used injection needles of the first invention wherein a movable member is mounted on a fixed member.
Figure 3:
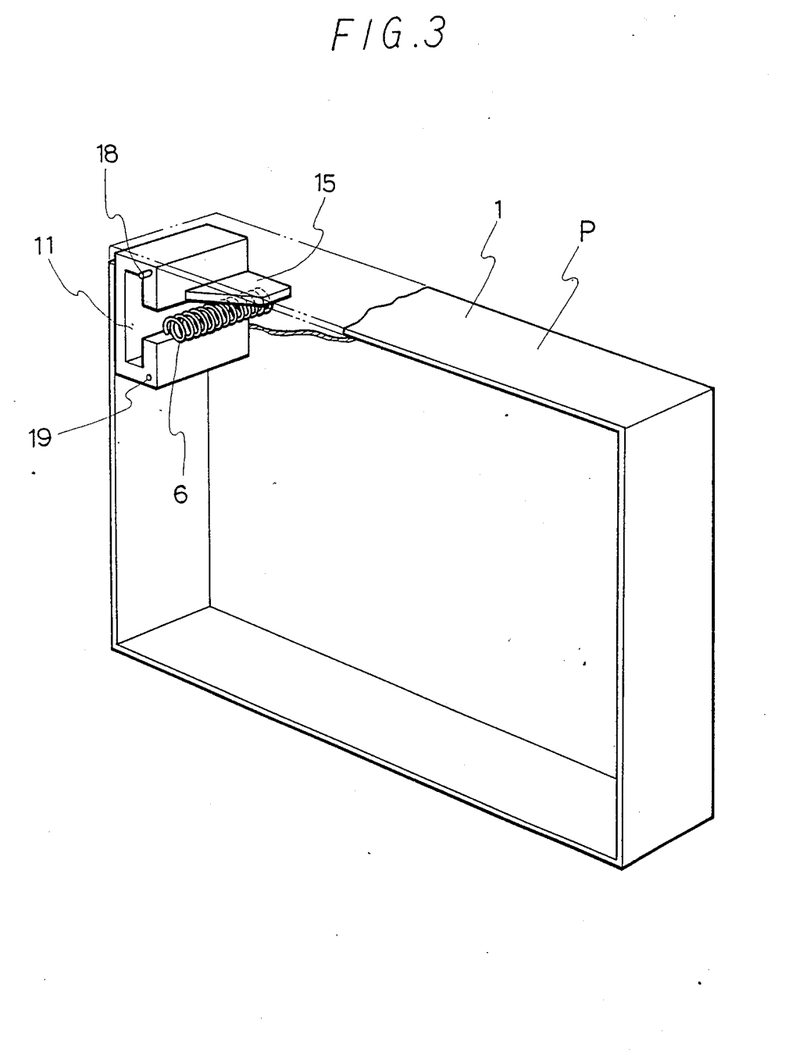
FIG. 3 is a partially-cutaway schematic perspective view of the other complementary half of the box of FIG. 1.
Figure 4:
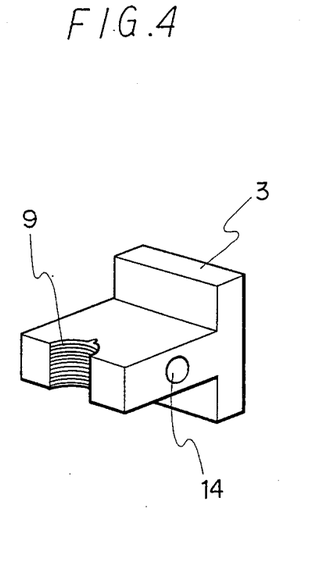
FIG. 4 is a schematic perspective view of an example of a movable member in the first invention.

In the embodiment shown in FIGS. 1 to 3, the case 1 is composed of two portions. The disposing box A (FIG. 5) is completed by combining the portion shown in FIG. 1 and the portion shown in FIG. 3.

A detaching means is arranged in the case 1. The functions of the detaching means are to hold the hub 22 of the injecton needle 21 inserted through the insertion opening 2, to remove the injection needle 21 from the syringe 20 by a prescribed operation, and to drop the injection needle 21, which is held by the movable member 3 and fixed member 4 in a removed state, into the case 1. The detaching means is, as described above, composed of the elastic means 6, movable member 3, rod 7 and fixed member 4 (see FIGS. 1 to 4).

Figure 2:
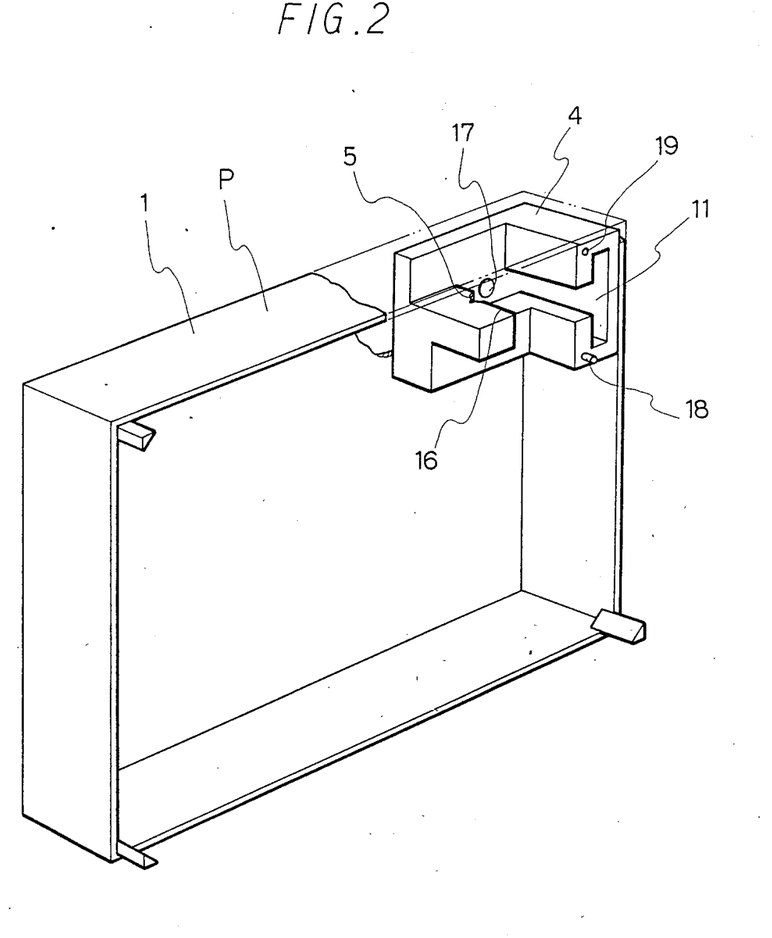
FIG. 2 is a partially-cutaway schematic perspective view of the embodiment of FIG. 1 showing the state wherein a movable member is not mounted on a fixed member.

The fixed member 4 positioning the movable member 3 at a prescribed place in the case 1 is fixedly arranged under the insertion opening 2 made in the case 1. The fixed member 4 has a holding portion 5 having a shape which corresponds to a part (about one-fourth) of a cross secton of the hub 22 as shown in FIG. 2. The holding portion 5 cooperates with the other holding portion 9 formed at the movable member 3 to hold the hub 22. Accordingly, the shape of the holding portions 5, 9 varies depending on the cross sectional shape of the hub 22 of the injection needle 21 to be discarded. In FIGS. 2 and 3, numeral 11 is a guide into which the movable member 3 is inserted. The fixed member 4 further has a notch 16 continuing to the holding portion 5. The notch 16 serves as a passage of the injection needle 21 when moving the injection needle 21 removed from the syringe 20 together with the movable member 3. As shown in FIG. 1, the notch 16 provides a clearance of about one-half of the diameter of the opening 12 between the movable member 3 and fixed member 4.

In the embodiment shown in FIGS. 1 to 3, the fixed member 4 is composed of two portions. These two portions are combined by inserting a projection 18 of the fixed member into the corresponding recess 19. The fixed member 4, however, might be composed of a single part.

The movable member 3 has a holding portion 9 of which shape corresponds to a part (about one-half) of a cross sectional shape of the hub 22. The hub 22 is firmly held by the holding portion 9 and holding portion 5 formed at the movable member 3 and fixed member 4 respectively. In that case, the hub 22 is firmly held by the holding portions 5, 9 when the hub is inserted in the opening 12, because the size of the opening 12 is a litle smaller than that of a cross section of the hub 22 and the hub 22 itself has elasticity, i.e. capability of shrinking a little in the radial direction. The movable member 3 is within the guide 11 and can move only in the direction parallel to that of elastic force of the elastic means 6. In the specification, "direction of elastic force of the elastic means" is a direction in which the elastic means returns to its original shape.

The elastic means 6 is fixed to or contacted with an end of the movable member 3. In the embodiment shown in FIG. 1, the end of a spring (elastic means) is so designed as to fit into a recess 14 formed at the movable member 3. The other end of the spring might be fixed to the case 1, or might be put on a projection formed on the inner surface of the case 1.

The elastic means 6 serves to keep the movable member 3 by its elastic force at such a position that the holding portion 9 of the movable member 3 and holding portion 5 of the fixed member 4 cooperate to form an opening 12 which corresponds to the cross sectional shape of the hub 22.

When an approximately trapezoid baffleplate 15 is installed on the fixed member 4 as shown in FIG. 3 in such a manner that an oblique side thereof contacts with the hub 22 moving with the movable member 3, the injection needle 21 can be securely dropped into the case even if the injection needle 21, which should be released from the contact with the fixing member 4 and dropped into the case 1, sticks to the holding portion 9 of the movable member 3 and would not drop into the case 1.

Figure 5:
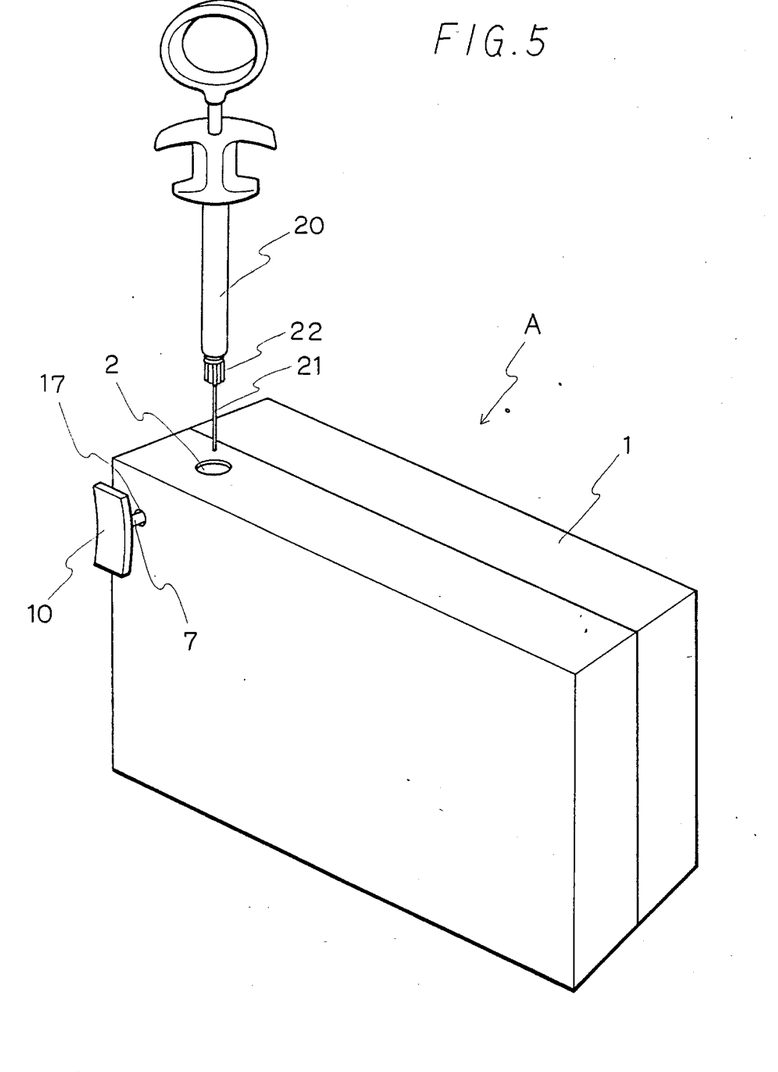
FIG. 5 is a view explaining the state wherein an embodiment of a box for disposing of used injection needles of the first invention is used.

As shown in FIG. 5, a rod 7 for moving the movable member 3 against elastic force of the elastic means 6 is fixed to or contacted with the end opposite to an end of the movable member 3 to which or with which the elastic means 6 is fixed or contacted. In the specification the term "rod" is a wide conception including bar members, plate members, and the like, and includes any member as long as it functions as a "rod" in the present invention. A part of the rod 7 protrudes outside the case 1 through a hole 17 (see FIG. 5) made in the case 1. At an end of the rod 7 protruding outside the case 1, there is preferably attached an approximately rectangular pressing plate 10 which is so curved as to fascilitate the pressing operation by a finger. After the arrangement of the rod 7 in the case 1, the pressing plate 10 can be attached to the end of the rod 7 protruding from the case 1 by means of adhesives or screws.

Next there is explained a method of removing a used injection needle from a syringe and thereafter containing the removed injection needle in a case with the use of a disposing box A of the present embodiment.

First the syringe 20 is inserted into the insertion opening 2 made in the case 1 to fit the hub 22 in the opening 12 defined by the holding portion 9 of the movable member 3 and the holding portion 5 of the fixed member 4 (see FIG. 5). The syringe 20 is rotated to release the screw connection between the injection needle 21 and syringe 20. Then the pulling out of the syringe 20 from the insertion opening 2 causes the injection needle 21 to be held by the movable member 3 and fixed member 4 and to remain in the case 1. In that case, the injection needle 21 is firmly held by the movable member 3 and fixed member 4 mainly due to elasticity of the hub 22 itself. Therefore even when an end of an injection needle (an end on the side of liquid drug) is pierced into a rubber plug and the like on the side of a syringe as in the case of, for example, double-edged injection needles, the pulling out of the injection needle 21 through the insertion opening 2 together with the syringe 20 due to the holding function of the rubber plug and the like hardly occurs.

The injection needle 21 removed from the syringe 20 and held by the movable member 3 and fixed member 4 can be dropped into and contained in the case 1 by pressing the plate 10 against the elastic force of the elastic means 6. In that case, the attachment of a baffleplate 15 to the fixed member 4 securely causes the injection needle 21 to be dropped into the case. Injection needles are contained in this way, and the box might be discarded when it is filled with used injection needles.

The disposing box of the present invention can be preferably used in discarding screw-type injection needles, or Lure-lock-type injection needles (i.e. injection needles which enable connection between injection needles and syringes by inserting the injection needles into connecting portions of the syringes and rotating a little in one direction). When used in discarding double-edged injection needles or blood-gathering needles among the above injection needles, the disposing box remarkably exhibits its convenience due to the holding effect of the holding portion.

Next there is explained the second invention.

Figure 6:
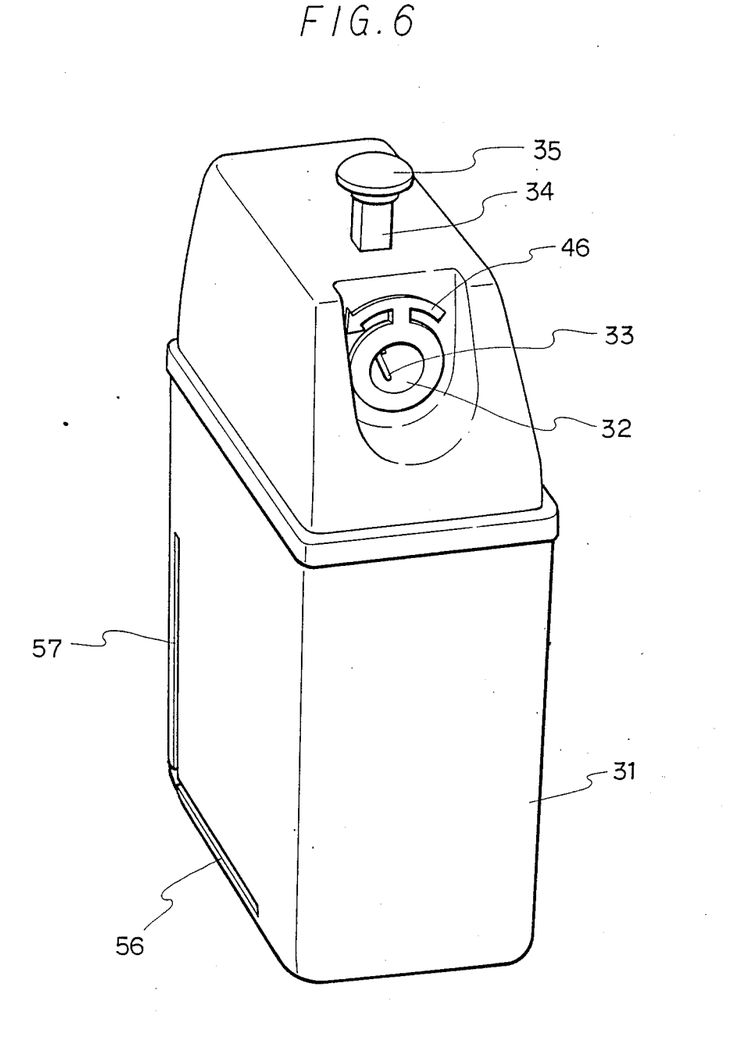
FIG. 6 is a schematic perspective view of the embodiment of a box for disposing of used injection needles of the second invention.

In FIG. 6, numerals 31, 32 and 33 are a case, a tubular guide hole and a slit, respectively. The case 31 serves to contain used injection needles removed from syringes, and is not particularly limited in its shape and size. As a material for the case 31, there can be preferably used the same materials as in the case 1 in the first invention.

A tubular guide hole 32 is laterally provided at the upper side wall of the case 31. The size of the guide hole 32 is large enough to enable insertion of a tip portion of a syringe, and is tapered down toward the inner part thereof. A slit 33 is formed at the under surface of the guide hole 32. The slit 33 has sufficient width and length to allow easy passage of a a needle of double-edged injection needle on the side of the liquid drug.

An operation rod 34 protrudes upwardly from the top surface of the case 31. A cap 35 is put on the tip of the operation rod 34. Above the opening of the guide hole 32, a mark 46 showing the rotational direction of a syringe inserted into the guidehole 32 is integrally formed with the guide hole 32.

A holding means 36 arranged at the inner part of the guide hole 32 is explained below with reference to FIGS. 7 and 8. The holding means 36 comprises a fixed member 37 and a movable member 38. The fixed member 37 is fixed to the case 31 through a bracket 41. The movable member 38 can slide up and down within a guide 42 fixed to the case 31. At the upper end of the movable member 38, the above-mentioned operation rod 34 is integrally formed with the movable member 38. A spring 43 is arranged between the bottom surface of the movable member 38 and the guide 42.

Figure 7:
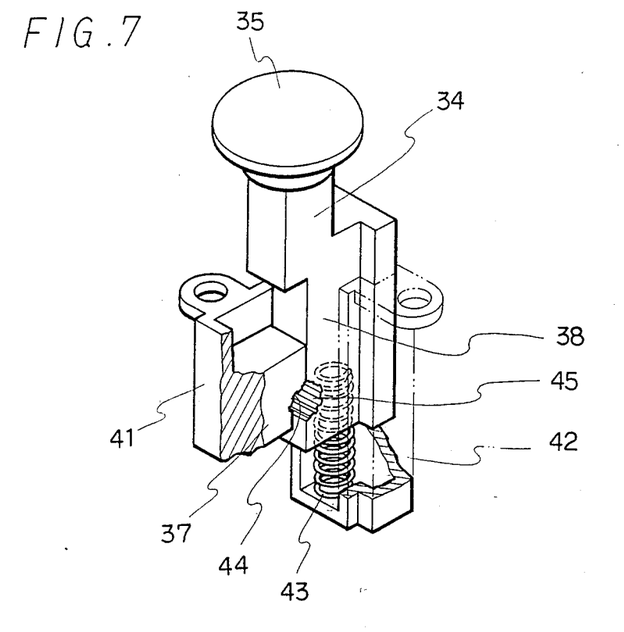
FIGS. 7 and 8 are schematic views showing the operation of a holding means in the second invention.

FIG. 7 shows the movable member 38 pressed upwardly by the spring 43. Holding portions 44 and 45 are formed respectively at such portions of the fixed member 37 and movable member 38 that face each other in the condition where the movable member 38 is pressed upwardly. Each holding portion 44, 45 has an arc-like contour so as to readily hold a hub of the injection needle, and has ribs at its surface to prevent the rotation of the hub.

Figure 8:
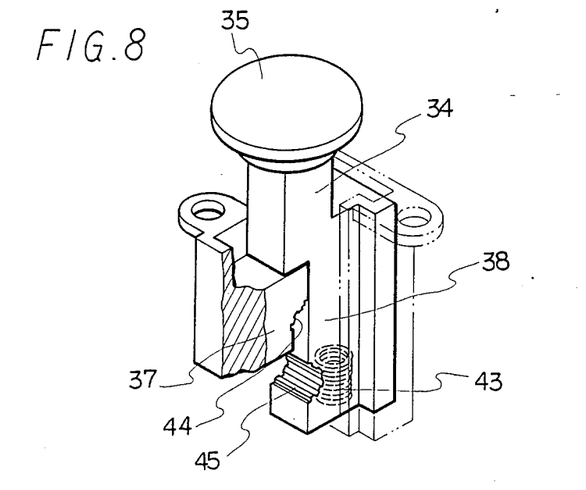

Since the movable member 38 is supported (pressed up) by the spring 43, the depressing of the operation rod 34 with a hand causes the movable member 38 to be depressed as shown in FIG. 8. In this depressed condition, the holding portions 44 and 45 separate from each other, so that the injection needle of which hub is held by the holding portions is released from such holding condition and dropped into the case.

Figure 9:
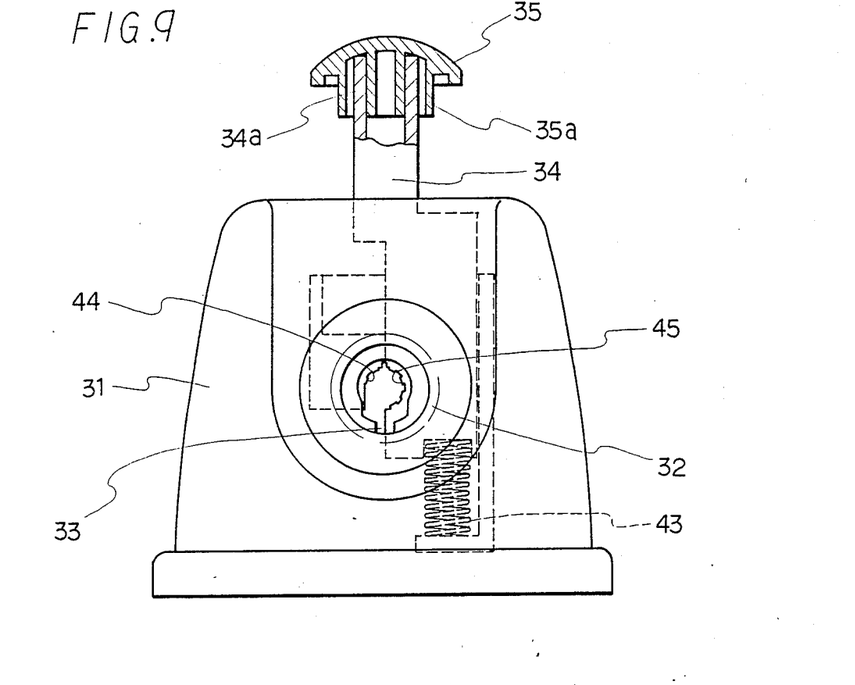
FIG. 9 is a front view of a guide hole and a holding means.
Figure 11:
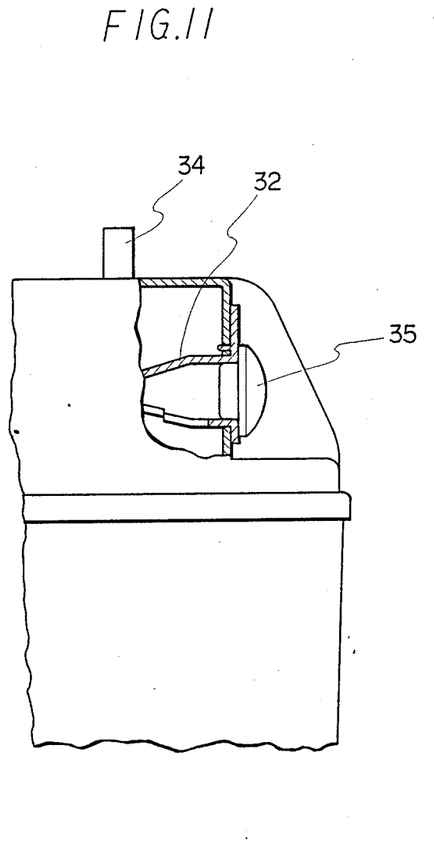
FIG. 11 is a partial sectional view showing the state wherein a cap is inserted into an opening of the guide hole.

FIG. 9 shows a cap 35 of which hub portion 35a is engaged with a tip portion 34a of the operation rod 34. The cap 5 is attachable to and detachable from the operation rod 34. The cap 35 is so made as to also tightly engage with an opening of the guide hole 32 as shown in FIG. 11. It is preferable to employ "close fit" in that engagement to prevent the cap 35 from accidentally slipping off from the guide hole 32.

Figure 12:
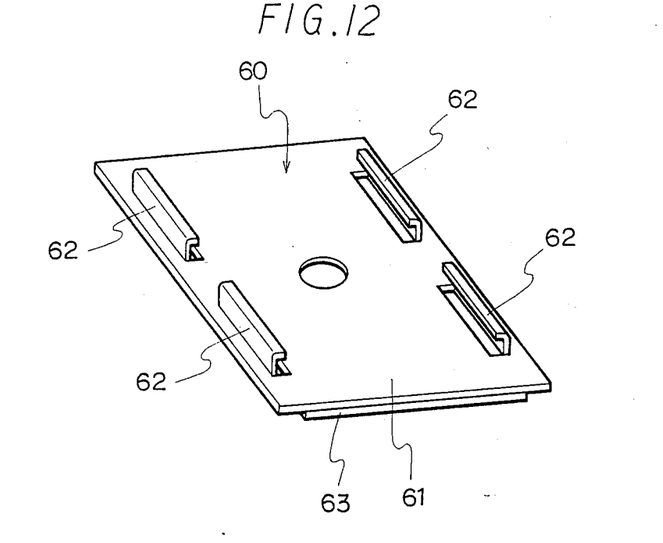
FIG. 12 is a perspective view of a fixing plate.
Figure 13:
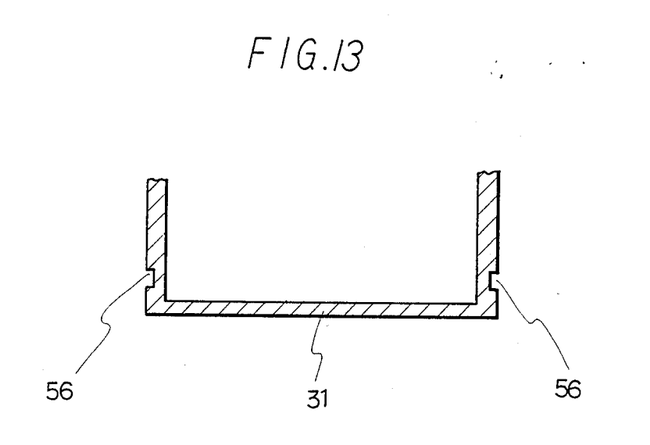
FIG. 13 is a sectional view showing grooves formed at the case.

Grooves 56, 57 are formed on the side wall of the case 31 near the bottom surface and back surface of the case 31 as shown in FIG. 6. The grooves 56 are formed on both side walls of the case 31 as shown in FIG. 13. The grooves 57 are also formed on both side walls of the case 31 (not shown). FIG. 12 shows a fixing plate 60 comprising a plate 61 which has approximately the same form as the bottom surface of the case 31 and has L-shaped engaging projections 62 at its four corners. The projections 62 engage with the grooves 56, 57 and slide therein. A suitable joining means, for example double-surface-adhering tape 63, is adhered to the back surface of the plate 61.

Figure 14:
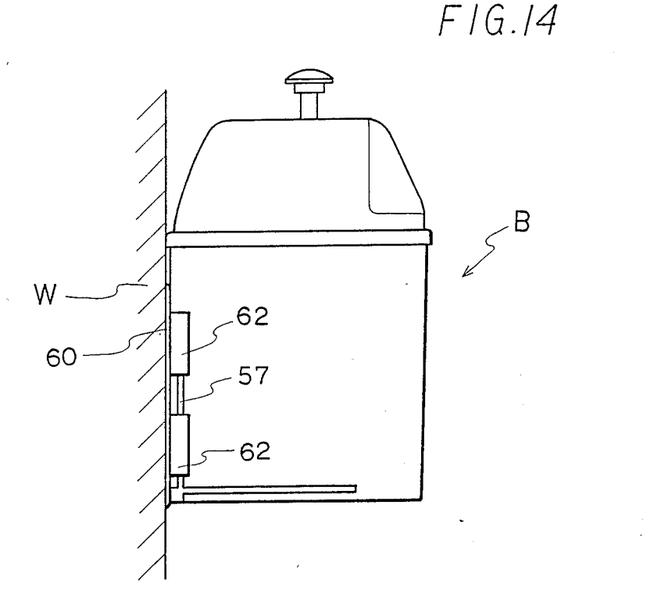
FIGS. 14 and 15 are side views showing the state of attachment of the case.
Figure 15:
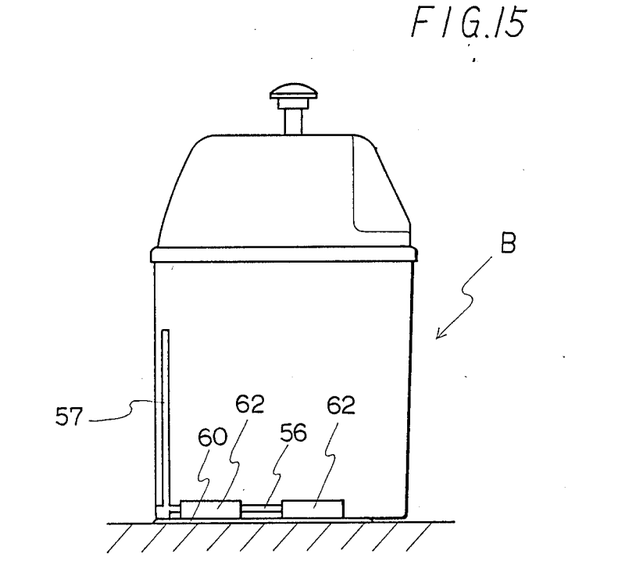

The disposing box B can be attached to a wall W by engaging the projection 62 of the fixing plate 60 with the grooves 57 as shown in FIG. 14. Further, the disposing box B can be attached to the floor or desk by engaging the projections 62 of the fixing plate 60 with the grooves 56 as shown in FIG. 15.

Next, there is explained a method of removing a used injection needle from a syringe and thereafter disposing of the removed injection needle in a case with the use of a disposing box B of the present embodiment.

Figure 10:
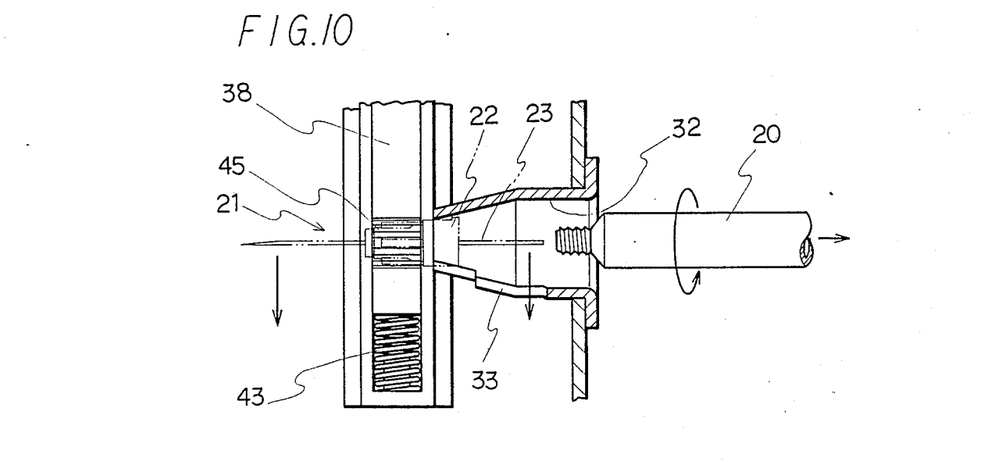
FIG. 10 is a longitudinal sectional view of a guide hole and a holding means.

First the syringe 20 is inserted into the guide hole 32 to fit the hub 22 in the opening defined by the holding portion 45 of the movable member 38 and the holding portion 44 of the fixed member 37 (see FIG. 10). The syringe 20 is rotated anticlockwise to release the screw connection between injection needle 21 and syringe 20. Then the pulling out of the syringe 20 from the guide hole 32 causes the injection needle 21 to be held by the movable member 38 and fixed member 37 and to remain in the case 31. In that case, the injection needle 21 is firmly held by the holding portion 45 of the movable member 33 and holding portion 44 of the fixed member 37 mainly due to the elasticity of the hub 22 itself. Therefore even when an end of an injection needle (an end on the side of liquid drug) is pierced into a rubber plug and the like on the syringe side as in the case of, for example, double-edged injection needles, the pulling out of the injection needle 21 through the guide hole 32 together with the syringe due to the holding force of the rubber plug and the like hardly occurs.

The injection needle 21 removed from the syringe 20 and held by the holding portions 44, 45 can be dropped into and contained in the case 31 by depressing the movable member 38 by using the operation rod 34. In that case, the injection needle 21 can be securely dropped into the case 31 since a needle 23 on the side of the liquid drug drops through the slit 33.

After the box is filled with the used injection needles removed from the syringes according to the method described above, the cap 35 is detached from the operation rod 34 and pressed into the opening of the guide hole 32, so that jumping out or protruding of contained injection needles from inside the case is prevented.

The disposing box of the present invention can be preferably used in discarding screw-type injection needles, or Lure-lock-type injection needles. When used in discarding double-edged injection needles or blood-gathering needles among the above mentioned injection needles, the disposing box remarkably exhibits its convenience due to the holding effect of the holding portion.

As explained above, there can be obtained the following effects according to the disposing box of the present invention.

(1) Since a target for the insertion of a used injection needle is larger than that in the conventional method of inserting an injection needle into a cap, there is no danger of pricking and injuring a handler's finger and the like by mistake even when inserting injection needles with a box in a hand. When injection needles are inserted into a box fixed to a suitable place, the danger of pricking hands and the like can be perfectly avoided.

(2) Used injection needles can be discarded together with a box, so that the discarding operation is very safe and hygienic, and there is no fear that the disposer is injured with an injection needle of which cap is of during the discarding operation of removed injection needles.

(3) Used injection needles can be removed by merely inserting injection needles into the insertion opening of the disposing box, which enables simple disposal of used injection needles in comparison with the conventional method using caps.

(4) Even when an end of an injection needle is pierced into a rubber plug and the like on the side of the syringe as in the case of double-edged injection needles, the pulling out of the injection needle, which is removed from the syringe, together with the syringe on pulling out the syringe from the case hardly occurs since the removed injection needle is firmly held by the holding portions. Thus the injection needles can be securely removed from syringes.

The second invention further gives the following effects in addition to the above effects (1) to (4).

(5) A slit is formed at the guide hole, so that even a double-edged injection needle can smoothly drop into the case and be easily contained in the case.

(6) The opening of the guide hold can be closed with a cap, which enables very safe and hygienic disposing operation.

What is claimed is:

1. A box for disposing of used injection needles comprising:
   (A) a tubular guide hole provided laterally at a box and enabling insertion of a tip portion of a syringe;
   (B) a slit formed at an under surface of the guide hole and enabling the drop of an injection needle;
   (C) a holding means for holding a hub of the injection needle screwed at a tip of the syringe, the means comprising a fixed member and a movable member and being located at the inner part of the guide hole;
   (D) an operation rod for pushing and moving the movable member to release the holding condition, a tip of the rod protruding outside the case; and
   (E) a cap capable of alternatively engaging with the tip of the operation rod and an opening of the tubular guide hole.

2. The box of claim 1, wherein at least one groove for attachment and detachment of a fixing plate is formed at a side wall of the case.

3. A box for disposing of used injection needles comprising:
   (A) a casing having an opening at its upper portion whereinto a tip portion of a syringe is capable of being inserted, and
   (B) an injection-needle-detaching means which is arranged in the case, and which removes an injection needle from the syringe inserted through the opening and drops into the case;
   (C) wherein the injection-needle-detaching means comprises:
      (a) a movable member having a first holding portion for holding a hub of the injection needle;
      (b) a fixed member fixed to the case and having a second holding portion for holding the hub of the injection needle in cooperation with the first holding portion of the movable member, and a notch continuing to the second holding portion of the fixed member to allow the movement of the hub, which is removed from the syringe and held by a holding portion defined by the first holding portion of the movable member and the second holding portion of the fixed member, together with the movable member;
      (c) an elastic means arranged in such a manner that the direction of elastic force thereof is parallel to the moving direction of the movable member, one end of the elastic means being fitted into a recess formed at the movable member; and
      (d) a rod for moving the movable member against the elastic force of the elastic means, a part thereof protruding outside the case;
   wherein the holding portion fits the shape of the hub and forms an opening of which size is a little smaller than that of a cross section of the hub.

4. The box of claim 3, wherein the elastic means is a spring.

* * * * *